US012252581B2

(12) United States Patent
Wang et al.

(10) Patent No.: US 12,252,581 B2
(45) Date of Patent: Mar. 18, 2025

(54) PREPARATION METHOD OF CARDANOL-MODIFIED POLYAMINE CURING AGENT WITH HIGH CORROSION RESISTANCE

(71) Applicant: Zhejiang Wansheng Co., Ltd, Zhejiang (CN)

(72) Inventors: Qiuwei Wang, Zhejiang (CN); Qi Gu, Zhejiang (CN); Xufeng Li, Zhejiang (CN); Jian Chen, Zhejiang (CN); Yunxing Lv, Zhejiang (CN)

(73) Assignee: Zhejiang Wansheng Co., Ltd, Zhejiang (CN)

( * ) Notice: Subject to any disclaimer, the term of this patent is extended or adjusted under 35 U.S.C. 154(b) by 641 days.

(21) Appl. No.: 17/523,886

(22) Filed: Nov. 10, 2021

(65) Prior Publication Data

US 2022/0064368 A1 Mar. 3, 2022

Related U.S. Application Data

(63) Continuation of application No. PCT/CN2021/096201, filed on May 27, 2021.

(30) Foreign Application Priority Data

Jun. 29, 2020 (CN) .......................... 202010602702.2

(51) Int. Cl.
*C09D 5/08* (2006.01)
*C07C 39/19* (2006.01)
*C08G 59/50* (2006.01)
*C09D 163/00* (2006.01)

(52) U.S. Cl.
CPC .......... *C08G 59/5033* (2013.01); *C07C 39/19* (2013.01); *C09D 5/08* (2013.01); *C09D 163/00* (2013.01)

(58) Field of Classification Search
None
See application file for complete search history.

(56) References Cited

U.S. PATENT DOCUMENTS

2009/0226729 A1* 9/2009 Niimoto .................. C09D 5/08
428/416

FOREIGN PATENT DOCUMENTS

| CN | 101177055 | 5/2008 |
| CN | 101333286 | 8/2011 |
| CN | 106046267 | 10/2016 |
| CN | 107973899 | 12/2019 |
| CN | 111763151 | 10/2020 |

OTHER PUBLICATIONS

English language machine translation of Xu Li et al., "Study on Synthesis of Cardanol Type Hexamethylenediamine Benzoxazine and Curing Behavior", Specialty Petrochemicals, Nov. 30, 2013, pp. 1-5 (Year: 2013).*
Xu Li et al., "Study On Synthesis of Cardanol Type Hexamethylenediamine Benzoxazine and Curing Behavior", Speciality Petrochemicals, with English abstract, Nov. 30, 2013, pp. 1-5.
"International Search Report (Form PCT/ISA/210) of PCT/CN2021/096201," mailed on Aug. 6, 2021, pp. 1-4.
"Written Opinion of the International Searching Authority (Form PCT/ISA/237) of PCT/CN2021/096201," mailed on Aug. 6, 2021, pp. 1-5.

* cited by examiner

*Primary Examiner* — Megan McCulley
(74) *Attorney, Agent, or Firm* — JCIP GLOBAL INC.

(57) ABSTRACT

The present invention discloses a preparation method of a cardanol-modified polyamine curing agent with high corrosion resistance. The method includes the following steps: subjecting cardanol, paraformaldehyde and an amine compound to Mannich reaction, after the Mannich reaction, adding a water-soluble initiator for polymerization reaction, then evaporating water and excessive amine compound under reduced pressure after the polymerization reaction, thus obtaining a cardanol-modified polyamine curing agent. The coating obtained by curing the curing agent with an epoxy resin has greatly improved chemical resistance and corrosion resistance, indicating that the use of the water-soluble initiator in this present invention enables olefins to be polymerized very well, and molecules are reinforced obviously after polymerization, thereby greatly improving the chemical resistance and corrosion resistance.

7 Claims, No Drawings

PREPARATION METHOD OF CARDANOL-MODIFIED POLYAMINE CURING AGENT WITH HIGH CORROSION RESISTANCE

CROSS-REFERENCE TO RELATED APPLICATION

This application is a continuation of international application of PCT application serial no. PCT/CN2021/096201 filed on May 27, 2021, which claims the priority benefit of China application no. 202010602702.2 filed on Jun. 29, 2020. The entirety of each of the above mentioned patent applications is hereby incorporated by reference herein and made a part of this specification.

FIELD OF TECHNOLOGY

The present invention relates to the technical field of organic synthesis, and in particular to a preparation method of a cardanol-modified polyamine curing agent with high corrosion resistance.

BACKGROUND

Cardanol is extracted from a cashew husk, and has a phenolic hydroxyl structure, and may substitute partial phenolic compounds to participate in chemical reaction; further, cardanol is a kind of renewable biological resource, capable of solving a part of petroleum energy crisis.

Due to renewability, cardanol may be developed and applied into lots of products. The major application of cardanol is the preparation of a cardanol curing agent; the prepared curing agent is cured with an epoxy resin to obtain a high-stability, high temperature resistant paint film easy to be operated at a low temperature; the paint film is mainly used as a coating of a paint film on steamship and containers.

For example, Chinese patent (CN101333286) has disclosed that cardanol, formaldehyde and polyamine are used for reaction, and dehydrated under reduced pressure after the reaction to obtain a cardanol-modified amine curing agent; such kind of curing agent molecule mainly includes monomolecular compounds; and the molecular double bond on the chain is very unstable. Therefore, the curing agent has poor corrosion resistance and the coating is easily inclined to turn yellow under light conditions for a long time, thereby influencing the appearance of the paint film.

Chinese patent (CN107973899) has disclosed that cardanol glyceryl ether and cardanol are added to be reacted with formaldehyde and polyamine, thus changing product performance, such as, the improvement of product color, and hardness. The patent may not radically solve the problems of product color and chemical corrosion resistance.

SUMMARY

Directed to the above problems existing in the prior art, the objective of the present invention is to provide a preparation method of a cardanol-modified polyamine curing agent with high corrosion resistance.

The preparation method of the cardanol-modified polyamine curing agent with high corrosion resistance is characterized in that the method includes the following steps: subjecting cardanol, paraformaldehyde and an amine compound to Mannich reaction, after the Mannich reaction, adding a water-soluble initiator for olefin polymerization reaction, and evaporating water and excessive amine compound under reduced pressure after the polymerization reaction, thus obtaining a cardanol-modified polyamine curing agent with high corrosion resistance;

where, the cardanol has the following structural formula:

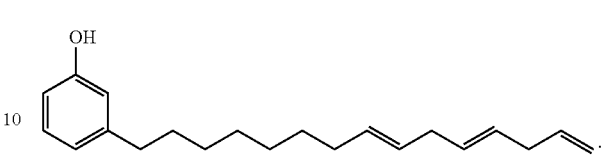

The preparation method of the cardanol-modified polyamine curing agent with high corrosion resistance is characterized in that a molar ratio of the cardanol the paraformaldehyde to the amine compound is 1:1-2:1.05-2.

The preparation method of the cardanol-modified polyamine curing agent with high corrosion resistance is characterized in that the amine compound is fatty an amine, an alicyclic amine or aromatic amine.

The preparation method of the cardanol-modified polyamine curing agent with high corrosion resistance is characterized in that the amine compound is one or a mixture of two of ethylenediamine, diethylenetriamine, triethylene tetramine, and tetraethylenepentamine.

The preparation method of the cardanol-modified polyamine curing agent with high corrosion resistance is characterized in that the Mannich reaction has a temperature of 30-85° C.

The preparation method of the cardanol-modified polyamine curing agent with high corrosion resistance is characterized in that the polymerization reaction temperature is 70-100° C. and the polymerization time is 3-5 h.

The preparation method of the cardanol-modified polyamine curing agent with high corrosion resistance is characterized in that the water-soluble initiator is an azobisisobutryamide hydrochloride, an azobisisobutryimidazoline hydrochloride, or an azoisobutyronitrile formamide, and a feed amount of the water-soluble initiator is 1-5% mass of the cardanol.

The preparation method of the cardanol-modified polyamine curing agent with high corrosion resistance is characterized in that in the step of evaporating water by distillation under reduced pressure after the reaction, a temperature is 50-90° C., and a vacuum degree is 10-50 KPa.

The preparation method of the cardanol-modified polyamine curing agent with high corrosion resistance is characterized by including the followings: adding cardanol and paraformaldehyde to a reactor according to a feed ratio, and slowly adding ethylenediamine dropwisely, controlling the dropwise addition temperature within 50-80° C. and the dropwise addition time within 2-2.5 h; afterwards, performing heat preservation for 3.5-4.5 h at 75-80° C., after the heat preservation, adding the water-soluble initiator, controlling a temperature within 95-100° C. and performing reflux reaction for 4-5 h, and cooling to room temperature to 80-85° C. after the reflux reaction, then performing distillation and dehydration at a vacuum degree of 10-15 KPa, thus obtaining a red brown solution, namely, the cardanol-modified polyamine curing agent with high corrosion resistance.

By the above technical solution, the present invention has the following beneficial effects compared with the prior art:

1) the present invention adopts a chemical polymerization method to change the proper characteristics of the cardanol-modified polyamine to greatly improve the stability; the high molecular weight compound is more stable than the single-molecular chain compound; the stability is specific in high chemical corrosion resistance and the like. Moreover, the present invention radically changes product performance and reduces the amount of low molecular weight compounds;

2) in the preparation method of the cardanol-modified polyamine curing agent, after Mannich reaction, a water-soluble initiator initiates for polymerization reaction directly without any special treatment, thereby avoiding the problem that lots of initiators are easily decomposed in contact with water to cause demanding conditions of polymerization reaction. Moreover, the present invention has good repeatability, simple operation and can achieve the stable and industrial production of raw materials for a curing agent;

3) in this present invention, the obtained high molecular weight compound is compounded with an epoxy resin to obtain a novel curing agent. Branched olefinic bonds in cardanol are subjected to polymerization reaction such that smaller molecules become a higher molecular weight compound, thus improving the stability. Therefore, the present invention can render the obtained curing agent to have high chemical corrosion resistance and yellowing resistance after light irradiation for a long time.

DESCRIPTION OF THE EMBODIMENTS

The following examples are used to specify the present invention, but are not construed as limiting the scope of the present invention.

Example 1

1500 kg cardanol and 300 kg paraformaldehyde were put to a reaction still, then dropwise addition of 450 kg ethylenediamine was started at room temperature, and a dropping speed was controlled during the dropwise addition; there was an obvious temperature rise; a temperature was 50-80° C. and dropping time was about 2 h; after the dropwise addition, the solution was thermally insulated for 4 h at 75-80° C., afterwards, 15 kg azobisisobutryamide hydrochloride were added to control a temperature of 95-100° C. for reflux reaction for 4-5 h; after the reflux reaction, the solution was cooled and dehydrated to a temperature of 80-85° C. with a vacuum degree of 10-15 KPa; after being dehydrated, the solution was red brown with an amine value/(mgKOH/g)=305 and a viscosity/mpa·S=25080.

Comparative Example 1

1500 kg cardanol and 300 kg paraformaldehyde were put to a reaction still, then dropwise addition of 450 kg ethylenediamine was started at room temperature, and a temperature was controlled to 50-80° C. and dropping time was about 2 h; after the dropwise addition, the solution was thermally insulated for 4 h at 75-80° C.; after the reaction, the solution was cooled and dehydrated to a temperature of 80-100° C. with a vacuum degree of 10-15 KPa; after being dehydrated, the solution was red brown with an amine value/(mgKOH/g)=310 and a viscosity/mpa·S=800.

Example 2

1500 kg cardanol and 305 kg paraformaldehyde were added to a reaction still, then dropwise addition of 450 kg ethylenediamine was started at room temperature, and a temperature was controlled to 75-80° C. and dropping time was about 2 h; after the dropwise addition, the solution was thermally insulated for 4 h at 75-80° C., afterwards, 20 kg azobisisobutryamide hydrochloride were added to control a temperature of 95-100° C. for reflux reaction for 4-5 h; after the reflux reaction, the solution was cooled and dehydrated to a temperature of 85-90° C. with a vacuum degree of 15-20 KPa; after being dehydrated, the solution was red brown with an amine value/(mgKOH/g)=308 and a viscosity/mpa·S=28100.

Example 3

3000 kg cardanol and 600 kg paraformaldehyde were added to a reaction still, then dropwise addition of 901 kg ethylenediamine was started at room temperature, and a temperature was controlled to 75-80° C. and dropping time was about 4 h; after the dropwise addition, the solution was thermally insulated for 5 h at 75-80° C., afterwards, 30 kg azobisisobutryamide hydrochloride were added to control a temperature of 95-100° C. for reflux reaction for 4-5 h; after the reflux reaction, the solution was cooled and slowly dehydrated to a temperature of 80-90° C. with a vacuum degree of 15-20 KPa; after being dehydrated, the solution was red brown with an amine value/(mgKOH/g)=300 and a viscosity/mpa·S=29400.

Example 4

1500 kg cardanol and 300 kg paraformaldehyde were added to a reaction still, then dropwise addition of 450 kg ethylenediamine was started at room temperature, and a temperature was controlled to 75-80° C. and dropping time was about 3 h; after the dropwise addition, the solution was thermally insulated for 5 h at 75-80° C., afterwards, 15 kg azobisisobutryimidazoline hydrochloride were added to control a temperature of 95-100° C. for reflux reaction for 4-5 h; after the reflux reaction, the solution was cooled and slowly dehydrated to a temperature of 75-80° C. with a vacuum degree of 10-15 KPa; after being dehydrated, the solution was red brown with an amine value/(mgKOH/g)=320 and a viscosity/mpa·S=28300.

Example 5

1500 kg cardanol and 290 kg paraformaldehyde were added to a reaction still, then dropwise addition of 450 kg ethylenediamine was started at room temperature, and a temperature was controlled to 75-80° C. and dropping time was about 3 h; after the dropwise addition, the solution was thermally insulated for 5 h at 75-80° C., afterwards, 15 kg azoisobutyronitrile formamide were added to control a temperature of 95-100° C. for reflux reaction for 4-5 h; after the reflux reaction, the solution was cooled and slowly dehydrated to a temperature of 75-80° C. with a vacuum degree of 10-15 KPa; after being dehydrated, the solution was red brown with an amine value/(mgKOH/g)=318 and a viscosity/mpa·S=32800.

Performance Test:

Samples in Examples 1-5 were subjected to curing reaction with an epoxy resin E51 by a conventional technique with a ratio of epoxy resin to a curing agent of 100:30; detection was performed according to the national testing standard of coating, and the detection result was shown in Table 1:

TABLE 1

Performance table of products after samples in Examples 1-5 were reacted with the epoxy resin E51

| Standard | Example 1 | Comparative Example 1 | Example 2 | Example 3 | Example 4 | Example 5 |
|---|---|---|---|---|---|---|
| Oil resistance | Normal | Color change | Normal | Normal | Normal | Normal |
| Oil-water resistance | Normal | Color-changed aqueous phase | Normal | Normal | Normal | Normal |
| Salt water resistance | Normal | A large amount of small bubbles | Normal | Normal | Normal | Normal |
| Distilled water resistance | Normal | A little of big bubbles | Normal | Normal | Normal | Normal |
| 5% sulfuric acid | Normal | Color-changed big bubbles | Normal | Normal | Normal | Normal |
| 12% NaOH | Normal | Swelling and color change | Normal | Normal | Normal | Normal |

Other Performance Test was Shown in Table 2:

TABLE 2

Performance table of products after samples of Examples 1-5 were reacted with the epoxy resin E51

| Performance test\Product name | Shock resistance/cm 50 cm back impact | Pencil hardness | Surface dry/Hard dry 5° C., 200 μm | Surface dry/Hard dry 25° C., 200 μm |
|---|---|---|---|---|
| Example 1 | Normal | 3H | 12/20 | 3.8/11.9 |
| Comparative Example 1 | Paint film rupture | H | 20/34 | 8/20 |
| Example 2 | Normal | 4H | 13/22 | 3.7/11.8 |
| Example 3 | Normal | 3H | 13/25 | 3.9/12.0 |
| Example 4 | Normal | 3H | 11/23 | 3.6/12.0 |
| Example 5 | Normal | 3H | 12/24 | 3.8/12.0 |
| Reference standard | GB/T 1732-93 | BG/T 6739-2006 | GB/T 1728-1979(1989) | |

It can be seen from the above Table 1 that the coating obtained by curing the cardanol-modified polyamine curing agent with high corrosion resistance obtained in the present invention with an epoxy resin has greatly improved chemical resistance and corrosion resistance. The result of Table 1 indicates that the water-soluble initiator may polymerize olefins very well; after polymerization, molecules are reinforced obviously to greatly improve chemical resistance and corrosion resistance, which has an obvious change relative to that of the prior polymerization; after polymerization, the viscosity/mpa·S is equal to 28300 around; the viscosity/mpa·S is equal to 800 around before polymerization. The obvious change of structural composition in the product will inevitably result in performance change.

It can be seen from the above Table 2 that the improved curing agent of the present invention may achieve 50 cm back impact property; but in Comparative Examples, the paint film is ruptured seriously. Further, the drying time is obviously improved to greatly expand the application scope of the curing agent.

What is claimed is:

1. A preparation method of a cardanol-modified polyamine curing agent with high corrosion resistance, characterized in that the method comprises the following steps: subjecting cardanol, paraformaldehyde and an amine compound to Mannich reaction, after the Mannich reaction, adding a water-soluble initiator to initiate olefin polymerization reaction, and evaporating water and excessive amine compound under reduced pressure after the olefin polymerization reaction, thus obtaining a cardanol-modified polyamine curing agent with high corrosion resistance, wherein a temperature for the olefin polymerization reaction is 70-100° C. and a time for the olefin polymerization reaction is 3-5 h;
wherein the water-soluble initiator is an azobisisobutryamide hydrochloride, an azobisisobutryimidazoline hydrochloride, or an azoisobutyronitrile formamide, and a feed amount of the water-soluble initiator is 1-5% mass of the cardanol;
wherein, the cardanol has the following structural formula:

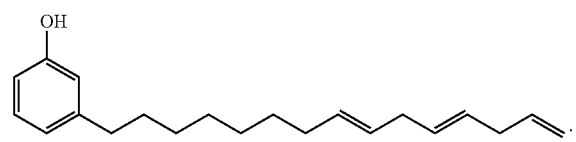 [SMILES: C=CC/C=C/C/C=C/CCCCCCCc1cccc(O)c1]

2. The preparation method of the cardanol-modified polyamine curing agent with high corrosion resistance according to claim 1, characterized in that a molar ratio of the cardanol, the paraformaldehyde to the amine compound is 1:1-2:1.05-2.

3. The preparation method of the cardanol-modified polyamine curing agent with high corrosion resistance according to claim 1, characterized in that the amine compound is an fatty amine, an alicyclic amine or an aromatic amine.

4. The preparation method of the cardanol-modified polyamine curing agent with high corrosion resistance according to claim 1, characterized in that the amine compound is one or a mixture of two of ethylenediamine, diethylenetriamine, triethylene tetramine, and tetraethylenepentamine.

5. The preparation method of the cardanol-modified polyamine curing agent with high corrosion resistance according to claim 1, characterized in that the Mannich reaction has a temperature of 30-85° C.

6. The preparation method of the cardanol-modified polyamine curing agent with high corrosion resistance according to claim 1, characterized in that the step of evaporating water under reduced pressure is done by distillation at a temperature of 50-90° C., and a vacuum degree of 10-50 KPa.

7. The preparation method of the cardanol-modified polyamine curing agent with high corrosion resistance according to claim 1, characterized by comprising the following steps: adding cardanol and paraformaldehyde to a reactor according to a feed ratio, and slowly adding ethylenediamine dropwisely at room temperature, controlling the dropwise addition temperature within 50-80° C. and the dropwise addition time within 2-2.5 h; afterwards, performing heat preservation to maintain a solution in the reactor at 75-80° C. for 3.5-4.5 h, after the heat preservation, adding the water-soluble initiator, controlling a temperature within 95-100° C. and performing reflux reaction for 4-5 h, and cooling to 80-85° C. after the reflux reaction, then performing distillation and dehydration at a vacuum degree of 10-15

KPa, thus obtaining a red brown solution, namely, the cardanol-modified polyamine curing agent with high corrosion resistance.

* * * * *